(12) United States Patent
Patel et al.

(10) Patent No.: US 12,332,133 B2
(45) Date of Patent: Jun. 17, 2025

(54) GROUND REACTION FORCE PLATE APPARATUS AND MEASUREMENT SYSTEM

(71) Applicant: UNIVERSITY OF CAPE TOWN, Cape Town (ZA)

(72) Inventors: Amir Patel, Cape Town (ZA); Callen Fisher, Plumstead (ZA); Liam James Clark, Rondebosch (ZA); James Teversham, Cape Town (ZA)

(73) Assignee: University of Cape Town, Cape Town (ZA)

( * ) Notice: Subject to any disclaimer, the term of this patent is extended or adjusted under 35 U.S.C. 154(b) by 420 days.

(21) Appl. No.: 17/756,230

(22) PCT Filed: Nov. 13, 2020

(86) PCT No.: PCT/IB2020/060685
§ 371 (c)(1),
(2) Date: May 19, 2022

(87) PCT Pub. No.: WO2021/099900
PCT Pub. Date: May 27, 2021

(65) Prior Publication Data
US 2022/0412824 A1    Dec. 29, 2022

(30) Foreign Application Priority Data
Nov. 22, 2019   (GB) ..................... 1917058

(51) Int. Cl.
*G01L 5/16*    (2020.01)
*A61B 5/00*    (2006.01)
(Continued)

(52) U.S. Cl.
CPC .............. *G01L 5/16* (2013.01); *A61B 5/1038* (2013.01); *A61B 5/6892* (2013.01);
(Continued)

(58) Field of Classification Search
CPC .. G01G 3/1414; G01G 21/244; A61B 5/1036; G01L 1/2206; G01L 1/2243; G01L 5/16; G01M 7/025; G01N 29/045
See application file for complete search history.

(56) References Cited

U.S. PATENT DOCUMENTS 3,640,130 A * 2/1972 Spescha ................. G01L 5/167
73/862.043
3,985,025 A * 10/1976 Ormond ................. G01L 1/2231
73/862.622
(Continued)

FOREIGN PATENT DOCUMENTS

| JP | 2001029329 A | 2/2001 |
| JP | 2008298486 A | 12/2008 |
| WO | 8402188 A1 | 6/1984 |

OTHER PUBLICATIONS

International Search Report and Written Opinion issued in PCT/IB2020/060685 mailed Jan. 22, 2021.
(Continued)

*Primary Examiner* — Tran M. Tran
(74) *Attorney, Agent, or Firm* — Heslin Rothenberg Farley & Mesiti P.C.

(57) ABSTRACT

A ground reaction force plate apparatus and measuring system are provided. The apparatus includes a plate for receiving a force to be measured as applied by a subject to the plate and a plurality of load cells in an arrangement supporting the plate, each load cell being a single-axis sensor with the axis provided at an angle to a plane of the plate and oriented towards a centre of the plate. The load cells are configured to measure data relating to a force vector at the angled single-axis sensor when the subject applies a force to the plate. A data collection controller is provided for logging time series measurements of the load cells over a time in which the subject applies a force to the plate. The
(Continued)

system applies machine learning processing to output the load cell measurements as a three-dimensional ground reaction force on the plate by a subject.

12 Claims, 5 Drawing Sheets

(51) Int. Cl.
*A61B 5/103* (2006.01)
*G01G 19/00* (2006.01)

(52) U.S. Cl.
CPC . *A61B 2562/0252* (2013.01); *A61B 2562/046* (2013.01); *G01G 19/00* (2013.01)

(56) References Cited

U.S. PATENT DOCUMENTS

| | | | | |
|---|---|---|---|---|
| 4,546,838 A * | 10/1985 | Ormond | ............... | G01G 3/1402 |
| | | | | 73/862.633 |
| 4,598,717 A * | 7/1986 | Pedotti | ................... | G06F 3/005 |
| | | | | 600/592 |
| 4,775,018 A * | 10/1988 | Kroll | ................... | G01G 3/1402 |
| | | | | 177/211 |
| 4,792,005 A * | 12/1988 | Olzog | ...................... | G01G 5/04 |
| | | | | 177/208 |
| 5,814,740 A * | 9/1998 | Cook | ...................... | G01L 5/164 |
| | | | | 73/862.637 |
| 6,354,155 B1 | 3/2002 | Berme | | |
| 6,699,207 B2 * | 3/2004 | Tasch | ................... | A61B 5/1038 |
| | | | | 600/587 |
| 7,320,455 B2 * | 1/2008 | Ryaboy | ................. | A47B 37/00 |
| | | | | 248/638 |
| 7,342,185 B2 * | 3/2008 | Haggstrom | ............... | G01L 1/26 |
| | | | | 73/862.627 |
| 8,315,823 B2 * | 11/2012 | Berme | .................... | G01L 25/00 |
| | | | | 702/41 |
| 8,453,512 B2 * | 6/2013 | Sasso | .................... | G01M 7/027 |
| | | | | 73/668 |
| 9,168,420 B1 * | 10/2015 | Berme | ................. | A61B 5/1036 |
| 9,255,859 B2 * | 2/2016 | Drueding | ............. | A61B 5/7235 |
| 9,310,282 B2 * | 4/2016 | Lee | .......................... | G01N 3/02 |
| 9,459,173 B2 * | 10/2016 | White | .................... | G01G 23/01 |
| 9,605,993 B2 * | 3/2017 | Ziebart | ................ | G01G 3/1414 |
| 9,880,066 B2 * | 1/2018 | Larsen | ..................... | G01L 5/16 |
| 9,927,310 B2 * | 3/2018 | Bryant | ................... | G01L 5/165 |
| 10,126,189 B2 * | 11/2018 | Castano Cano | ........ | G01L 5/167 |
| 10,527,508 B2 * | 1/2020 | Berme | ................. | G01L 1/2281 |
| 10,589,431 B2 * | 3/2020 | Nakayama | .............. | B25J 9/047 |
| 10,704,973 B2 * | 7/2020 | Drueding | ............. | A61B 5/1038 |
| 11,084,174 B2 * | 8/2021 | Saunders | ................. | B25J 5/007 |
| 2004/0158174 A1 * | 8/2004 | Tasch | ...................... | A61B 6/50 |
| | | | | 600/595 |
| 2009/0062695 A1 * | 3/2009 | Sauvignet | ............ | A61B 5/1038 |
| | | | | 600/592 |
| 2013/0144437 A1 | 6/2013 | Lee et al. | | |
| 2014/0150593 A1 * | 6/2014 | Brown | .................. | B25J 9/0045 |
| | | | | 901/19 |
| 2015/0283486 A1 | 10/2015 | Kim et al. | | |
| 2016/0169821 A1 * | 6/2016 | Meyer | ..................... | B22F 12/30 |
| | | | | 425/136 |
| 2019/0078951 A1 | 3/2019 | Berme et al. | | |
| 2021/0321905 A1 * | 10/2021 | Kim | ..................... | A61B 5/1128 |

OTHER PUBLICATIONS

P. Daponte et al., "Artificial neural networks in measurements", Measurement 23 (1998), pp. 93-115, Elsevier.

Z. Borden et al., "Force Plate," https://www.jontse.com/portfolio/forceplate.html, Aug. 5, 2020.

* cited by examiner

GROUND REACTION FORCE PLATE APPARATUS AND MEASUREMENT SYSTEM

CROSS REFERENCE TO RELATED APPLICATIONS

This application is a U.S. National Phase filing under 35 U.S.C. § 371 of International Application PCT/IB2020/060685, filed Nov. 13, 2020, and published as WO 2021/099900 A1 on May 27, 2021. PCT/IB2020/060685 claims priority from Great Britain patent application number 1917058.8, filed Nov. 22, 2019. The entire contents of each of these prior applications are hereby incorporated herein by reference.

FIELD OF THE INVENTION

This invention relates to a ground reaction force plate apparatus and measurement system. The invention may find application in the field of biomechanical analysis.

BACKGROUND TO THE INVENTION

Biomechanics relates to the study of the mechanical laws relating to the movement or structure of living organisms. Subfields of biomechanics include kinesiology, animal locomotion and gait analysis, musculoskeletal and orthopaedic biomechanics, sports biomechanics and the like.

Ground reaction force (GRF) is the force exerted by the ground on a body in contact with it. A person standing motionless on the ground exerts a contact force on it equal to the person's weight and at the same time an equal and opposite ground reaction force is exerted by the ground on the person. GRF is used in biomechanics to evaluate a subject's ability to exert force and power. This may be used in many applications.

Three-dimensional ground reaction force plates are known in biomechanics and robotics, which use multiaxial load cells. Multiaxial load cells use strain gauges that rely on the use of the material properties (such as stress and strain) to determine the force and therefore require a complex form of analysis. These multiaxial load cells are very expensive especially when more than one load cell is needed to achieve the desired force plate. These complex plates are not easily scalable to larger applications, such as a full-length running track.

Low-cost ground reaction force plates are known in the form of a plate with four uniaxial load cells at the corners, with the load cells arranged vertically. However, these plates only measure force in the vertical direction and therefore provide limited information.

There is accordingly scope for improvement. The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

According to a first aspect of the present invention there is provided a ground reaction force plate apparatus comprising: a plate for receiving a force to be measured as applied by a subject to the plate; a plurality of load cells provided in an arrangement supporting the plate, wherein each load cell is a single-axis sensor with the axis provided at an angle to a plane of the plate and oriented towards a centre of the plate and configured to measure data relating to a force vector at the angled single-axis sensor when the subject applies a force to the plate; and a data collection controller for logging time series measurements of the load cells over a time period in which the subject applies a force to the plate.

Further features may provide for the apparatus to include: a plurality of position sensors for detecting a position of the subject applying a force to the plate; and wherein the data collection controller is configured to log time series measurements of the position sensors over the time period in which the subject applies a force to the plate. Further features may provide for the apparatus to include a temperature sensor for measuring an ambient temperature at a time of the load cell measurements and including the temperature in the logged time series measurements of the load cells.

In one embodiment, the plate is a rectangular plate with four load cells provided at corners of the plate supporting the plate. In an alternative embodiment, the plate is a hexagonal plate with six load cells associated with each of six sides of the hexagonal plate supporting the plate Each load cell may be a single-axis sensor with the axis provided at an angle of between 30 degrees and 60 degrees to the plane of the plate, preferably at an angle of 45 degrees.

Further features may provide for the position sensors to be provided in the form of a grid of mechanical switches or in the form of optical position sensors.

Further features may provide for a plurality of plates to be disposed in an adjacent arrangement for sensing of data of a subject applying sequential forces to the plurality of plates.

According to another aspect of the present invention there is provided a ground reaction force measuring system comprising: a processor and a memory configured to provide computer program instructions to the processor to execute functions of components of the system; a data receiving component for receiving sensor data from a ground reaction force plate apparatus including force vector measurements of a plurality of load cells each in the form of a single-axis sensor with an axis provided at an angle to a plane of a plate of the apparatus receiving a force applied by a subject and oriented towards a centre of the plate; and a machine learning component for processing by machine learning the force vector measurements for mapping non-linear functions to evaluate a three-dimensional ground reaction force on the plate by a subject.

Further features may provide for the data receiving component to also receive position data for a position of a subject on the plate at the time of the force vector measurements and temperature data for the ambient temperature at the time of measurement.

Further features may provide for the machine learning component to include processing by machine learning the force vector measurements for mapping non-linear functions to evaluate a centre of pressure of the force on the plate by a subject.

The system may be a combined system including one or more ground reaction force plate apparatus as defined in the first aspect of the present invention.

According to another aspect of the present invention there is provided a computer-implemented method for measuring ground reaction force comprising: receiving sensor data from a ground reaction force plate apparatus including force vector measurements of a plurality of load cells each in the form of a single-axis sensor with an axis provided at an angle to angled plane of a plate of the apparatus receiving a force applied by a subject and oriented towards a centre of the plate; and processing by machine learning the force vector measurements for mapping non-linear functions to evaluate the three-dimensional ground reaction force on the plate by a subject.

Further features may provide for processing by machine learning the force vector measurements for mapping non-linear functions to also evaluate a centre of pressure of the force on the plate by a subject.

The processing by machine learning may include applying a deep neural network with the force vector measurements input into an input layer of the deep neural network, including training the deep neural network with known output values for each set of training input values, and including testing a trained deep neural network on unseen test input values and measuring error measurements to ensure predictive accuracy.

Embodiments of the invention will now be described, by way of example only, with reference to the accompanying drawings.

DETAILED DESCRIPTION WITH REFERENCE TO THE DRAWINGS

A ground reaction force plate apparatus is described in which a plate is provided for receiving a force to be measured, such as a force from a foot of a subject. The plate has uniaxial load cells arranged to support the plate with the load cells each arranged diagonally at an angle towards the center of the plate. The data gathered by the uniaxial or single-axis load cells is processed by a machine learning algorithm to calculate three-dimensional force vector measurements providing a three-dimensional ground reaction force. In one embodiment, the plate also includes position sensors for sensing a position of the force being applied, such as detecting a foot position. In another embodiment, the machine learning algorithm may also determine a center of pressure of the applied force from the load cell data.

By mounting the uniaxial load cells at an angle, this allows them to perceive components of the three-dimensional force vector as opposed to only the z-axis which vertically mounted load cells would measure. This allows the system to sense the three-dimensional force applied by the subject. As this method uses the bending or torque and the force experienced by the load cells, which is highly non-linear, this cannot be interpreted by a straight-forward mechanical model. Therefore, the system uses machine learning approaches to evaluate the data.

Figure 1:
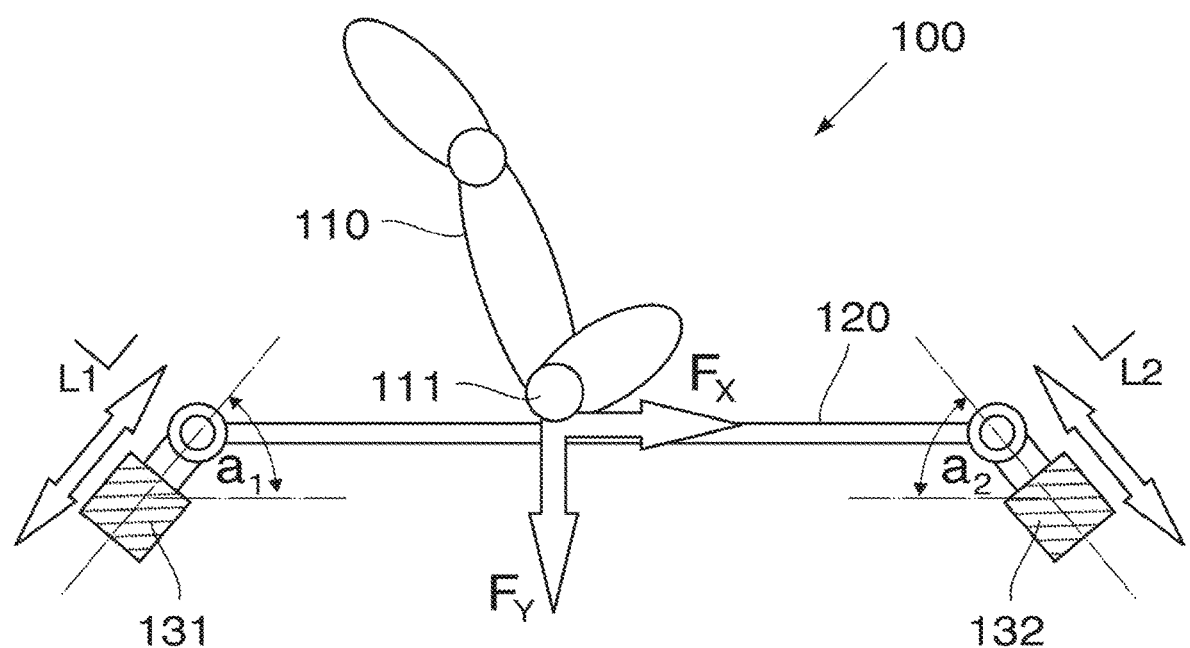
FIG. 1 is a schematic diagram which provides a two-dimensional illustration of a concept in accordance with the present disclosure.

Referring to FIG. 1, a schematic diagram (100) illustrates the concept on which the described ground reaction force plate apparatus is based. The concept is illustrated in a two-dimensional case for simplicity.

The diagram (100) shows a side view of a plate (120) on which a force is to be measured in the form of a foot (111) attached to a leg (110) of a subject. The plate (120) is shown as supported by two single-axis load cells (131, 132) each of which have their axes at angles to the plane of the plate (120). The angles are shown as ($\alpha_1$, $\alpha_2$) and in this case are identical.

The force applied by the subject's foot (111) is shown as ($F_x$, $F_y$) and is transferred to the two single-axis load cells (131, 132). In the ideal case, this can be modelled as:

$$F_{GRF} = \begin{bmatrix} F_x \\ F_y \end{bmatrix} = A \begin{bmatrix} V_{L1} \\ V_{L2} \end{bmatrix} = A V_L$$

With $V_{L1}$ and $V_{L2}$ being the forces in the axes of the load cells (131, 132).

However, in practice A is not constant and the relationship is actually:

$$F_{GRF} = f(\theta, V_L),$$

where θ represents a vector of unknown parameters and f is some non-linear function. In practice f is highly non-linear due to the following factors:
Manufacturing tolerances (misalignment);
Temperature effects;
Cross-coupling; and
Inaccuracy of load cell measurements.

Machine learning presents a viable method for mapping highly non-linear functions and can be utilised to calibrate the sensors of the ground reaction force plate apparatus. This may include training of a neural network which by means of a mechanical rig providing known forces to known positions. Additionally, human or animal subjects could apply forces by running/walking on the device while wearing an existing force sensor. These will then also be used as training data for the neural network.

Figure 2:
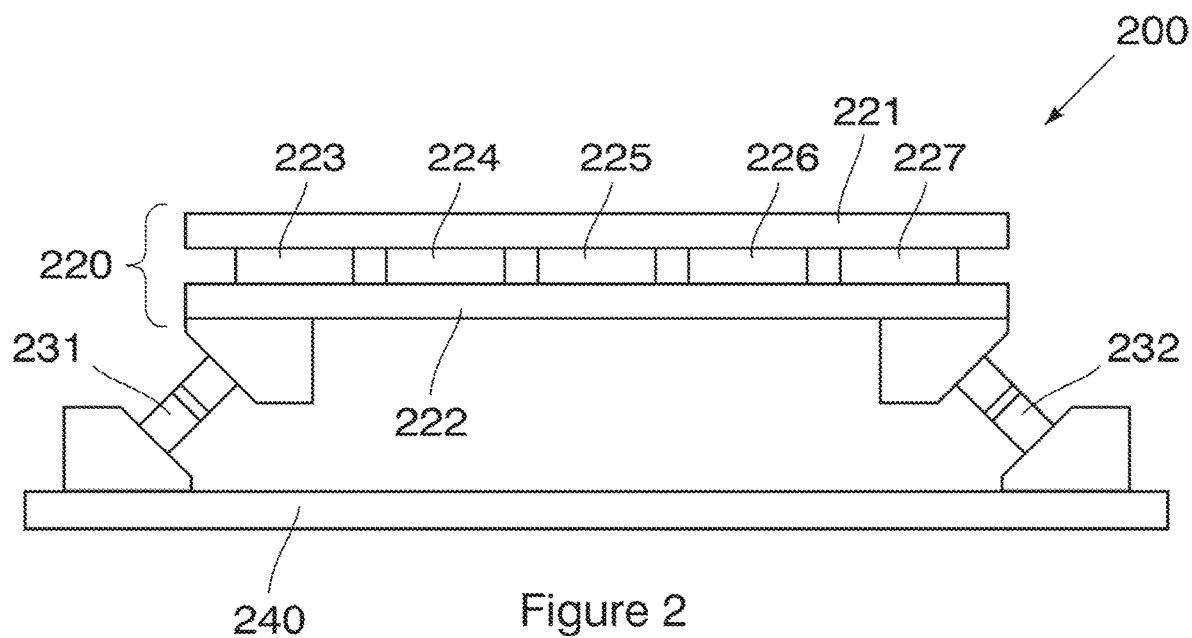
FIG. 2 is a side view of a ground reaction force plate apparatus according to aspects of the present disclosure.
Figure 3:
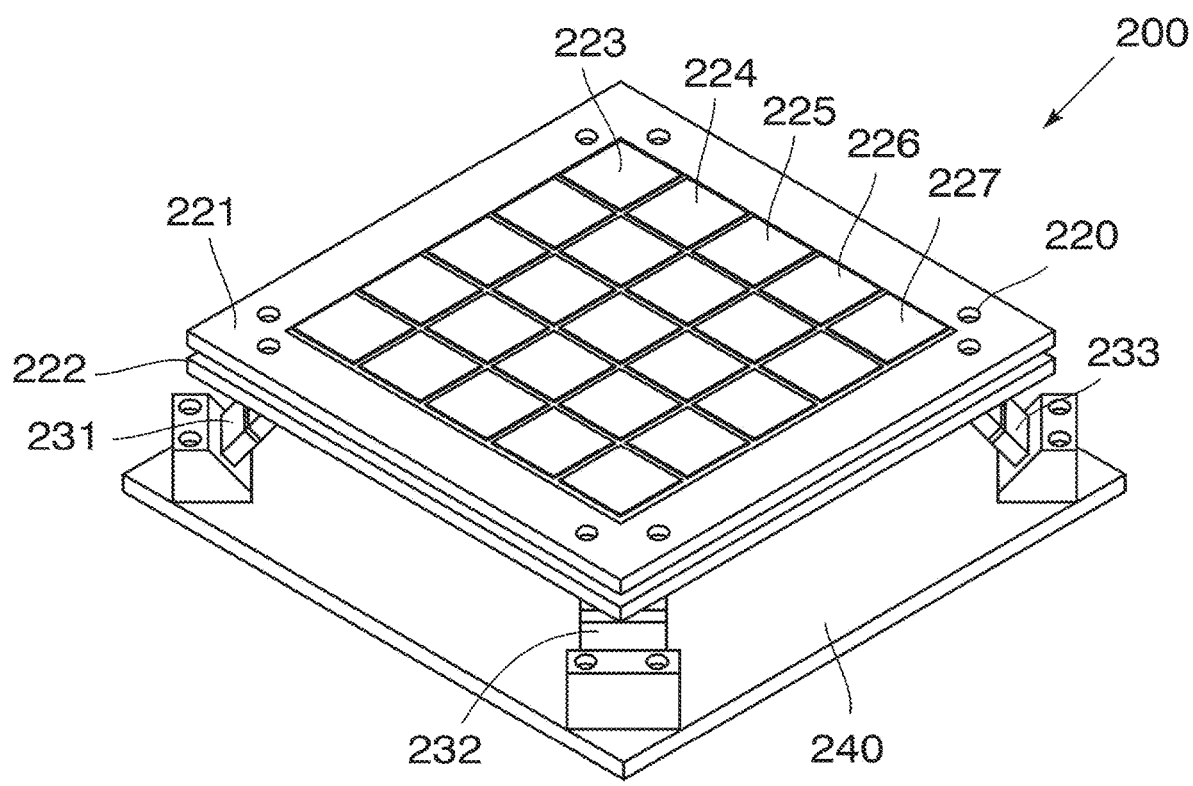
FIG. 3 is a perspective view of a ground reaction force plate apparatus according to aspects of the present disclosure.

Referring to FIGS. 2 and 3, a side view and a perspective view are shown of an example embodiment of a ground reaction force plate apparatus (200).

The apparatus (200) includes a plate (220). In this embodiment, the plate (220) has an upper plate member (221) and a parallel lower plate member (222). A grid of mechanical switches (223, 224, 225, 226, 227) provide position sensors which are activated by a force on the upper plate member (221) and are disposed between the upper and lower plate member (221, 222). An alternative to the mechanical switches may be the user of optical position sensors for sensing a subject applying a force to the plate (220).

The apparatus (200) includes a base support (240) on which four single-axis load cells (231, 232, 233, 234) are mounted, which support the plate (220). The load cells (231, 232, 233, 234) are provided at the four corners of the plate (220) and are provided at an angle to the vertical and angled towards a centre of the plate (220). In this example embodiments, the load cells (231, 232, 233, 234) are provided between the range of 30 degrees and 60 degrees to the plane of the plate (220), preferably, at 45 degrees, and at 90 degrees to adjacent load cells. If the base support (240) is provided on a horizontal surface, the angle of the load cells (231, 232, 233, 234) may be measured as between 30 degrees and 60 degrees to the vertical, preferably, at 45 degrees.

Figure 4:
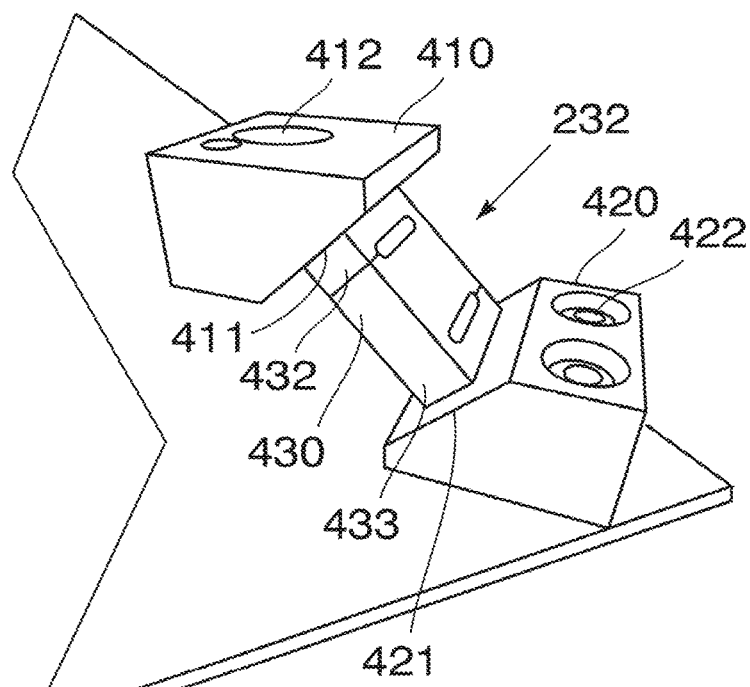
FIG. 4 is a perspective view of a detail of a single-axis sensor of the apparatus of FIG. 3.

FIG. 4 shows a more detailed perspective view of a load cell (232) with the plate (220) not shown. The load cell (232) has an upper bracket (410) for attachment of the load cell (232) to the plate (220). The upper bracket (410) has an attachment means (412) for attachment to an underside of the plate (220) and an angled side (411) for attachment to the load cell mechanism (430).

The load cell (232) has a lower bracket (420) for attachment of the load cell (232) to the base support (240). The lower bracket (420) has an attachment means (422) for attachment to an upper side of the base support (240) and an angled side (421) for attachment to the load cell mechanism (430). The load cell mechanism (430) includes two portions (432, 433) between which a load is measured when the load cells (232) are excited by a ground reaction force on the plate (220). The load cells (232) in this example are standard S-Type devices which measure force by means of strain gauges mounted in a particular pattern. The reason for the use of S-type cells is that they are capable of measuring compression and tension which are required to fully represent the 3D ground reaction forces.

The ground reaction force plate apparatus (200) provides an accurate, robust and inexpensive force plate. This may be provided as a portable device. It is straightforward to scale the apparatus to a force plate covering a larger area, such as an expanse of a track on which a subject may be evaluated whilst running or walking. Multiple apparatuses (200) may be used together to provide a larger force receiving area.

The described plate utilizes low-cost, single-axis load cells, mounted in a specific configuration to sense the full three-dimensional ground reaction force vector. The use of four single-axis load cells and low-cost electronic components can provide a system two orders of magnitude cheaper than current 3D force plates. Due to the affordability of the described system, multiple force plates can be employed by researchers for more complete tests. This will allow subjects to behave more naturally as they will be less constrained to perform a task on a specific, confined area.

Figure 8:
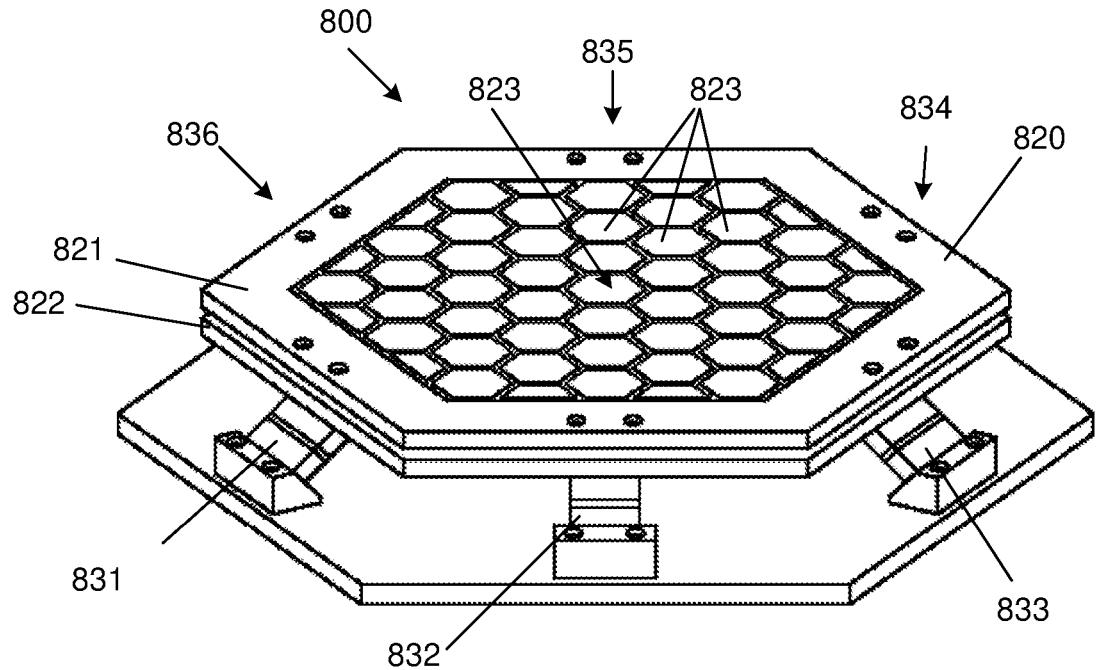
FIG. 8 is a perspective view of an alternative embodiment of a ground reaction force plate apparatus according to aspects of the present disclosure.

Although the example embodiment is shown with a rectangular plate (220), other shapes may be used with appropriate arrangements of angled sensors with the data calibration learnt by the machine learning processing from the measured tension and compression of the specific geometric configuration. For example, FIG. 8 shows a ground reaction force plate apparatus (800) according to an alternative embodiment in which a plate (820) is hexagonal and includes six single-axis load cells (831, 832, 833, 834, 835, 836) each associated with one of six sides of the hexagonal plate (820). In this example, the load cells (831, 832, 833, 834, 835, 836) are mounted mid-way between each side of the plate (820) but they may also be mounted at a corner of each of the six corners of the hexagonal plate (820). The plate (820) includes an upper plate member (821) and a parallel lower plate member (822) with a grid of mechanical switches (823) disposed between the upper and lower plate member (821, 822) providing position sensors which are activated by a force on the upper plate member (821) in the same way as described with reference to FIGS. 2 and 3. The mechanical switches (823) are shown here as hexagonal but they could also be rectangular or another suitable shape. The six single-axis load cells (831, 832, 833, 834, 835, 836) are provided at an angle to the vertical and angled towards a centre (840) of the plate (820). The load cells may be mounted in a similar way as described with reference to FIGS. 2 and 3.

Figure 5:
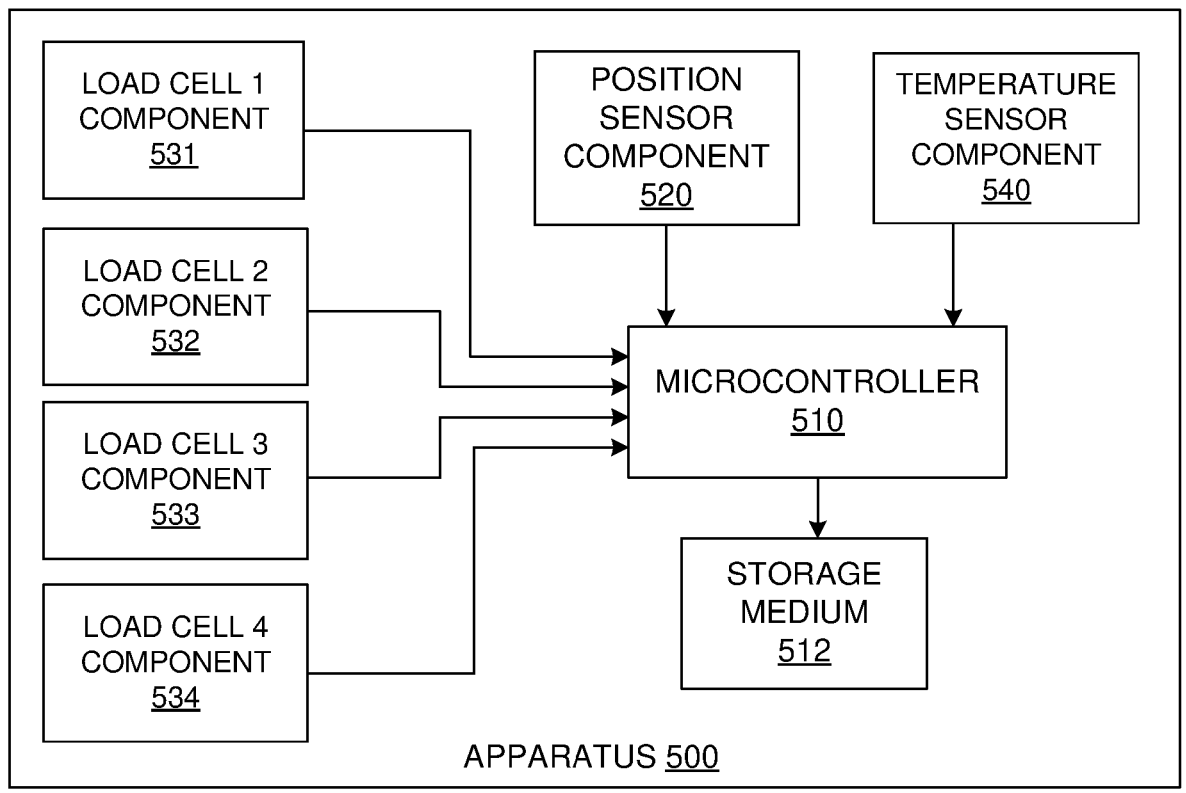
FIG. 5 a block diagram of the hardware components of a ground reaction force plate apparatus.

Referring to FIG. 5, a block diagram illustrates the hardware components of an example embodiment of a ground reaction force plate apparatus (500) according to embodiments of the disclosure.

The apparatus (500) includes the electronic components of the load cells (531, 532, 533, 534), and the electronic components of the position sensors (520). In addition, the apparatus (500) includes an electronic component of a temperature sensor (540) for measuring an ambient temperature at a time of receiving the force. The temperature at each load cell can be measured using a voltage-based temperature sensor.

A data collection controller in the form of a microcontroller (510) is provided for logging data produced by the position sensors, single-axis sensors of the load cells, and temperature sensor during an application of a force to the plate by a subject. The microcontroller (510) may store logged data to a storage medium (512) which may be transferred for processing by a computing device. In one embodiment, the force sensors may be measured at 1 kHz to a microcontroller and logged to a non-volatile memory device such as a secure digital card.

Figure 6:
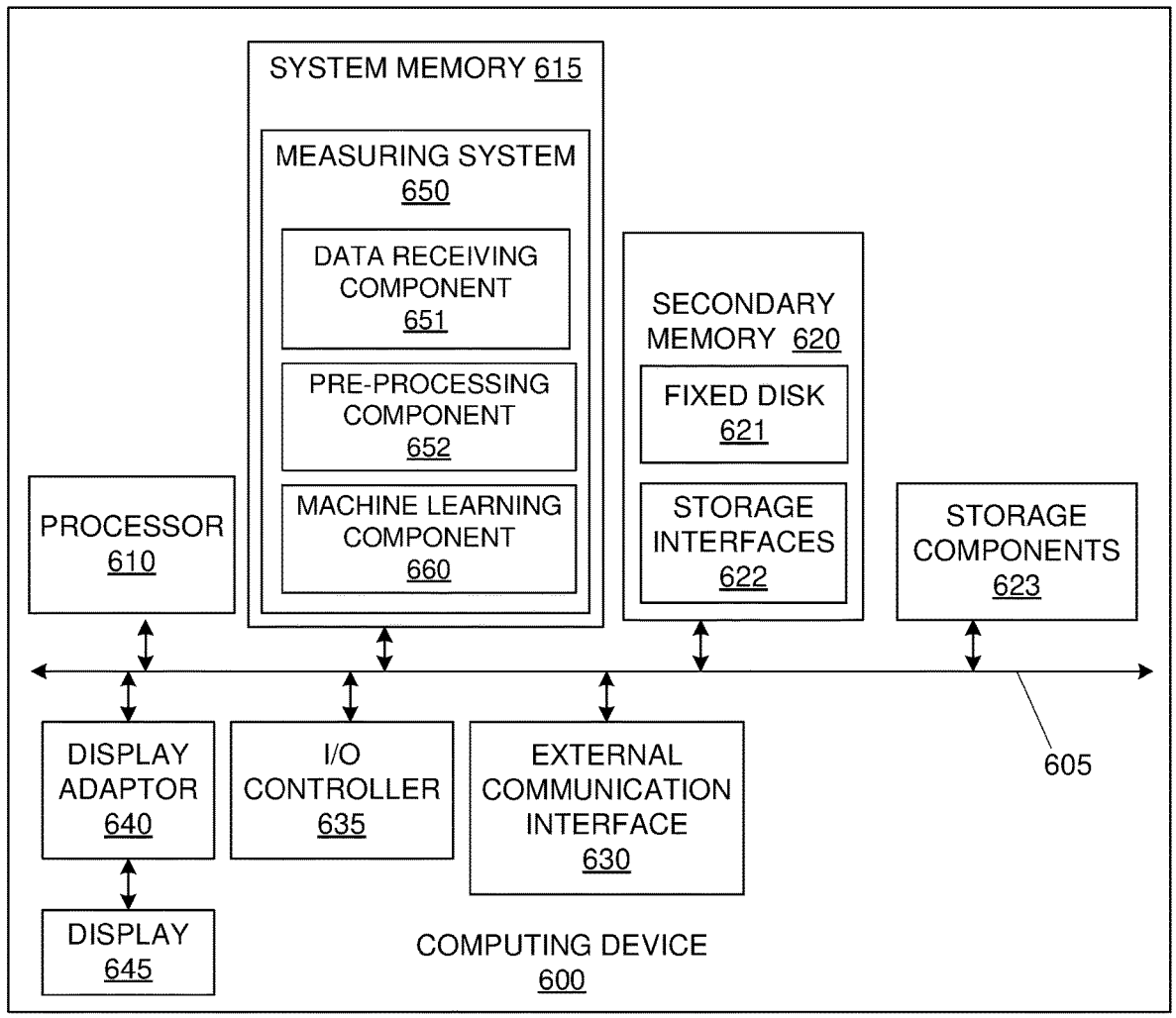
FIG. 6 is a block diagram of an example of a computing device in which various aspects of the disclosure may be implemented.

Referring to FIG. 6, an example of a computing device (600) is shown in which the processing of a ground reaction force measuring system (650) may be implemented.

The computing device (600) may include a processor (610) for executing the functions of the ground reaction force measuring system (650), which may be provided by hardware or by software units executing on the computing device (600).

The ground reaction force measuring system (650) may include a data receiving component (651) for receiving sensor data from a ground reaction force plate apparatus including force vector measurements of the load cells each in the form of a single-axis sensor with an axis provided at an angle to the vertical and angled towards a centre of a plate receiving a force applied by a subject.

The ground reaction force measuring system (650) may include or access remotely a machine learning component (660) for processing by machine learning the force vector measurements for mapping non-linear functions to evaluate the three-dimensional ground reaction force on the plate by a subject. The measuring system (650) may include a pre-processing component (652) for normalizing and, optionally, filtering the received sensor data for input into a neural network of the machine learning component (660).

The machine learning component (660) may train a neural network to calibrate the ground reaction force plate apparatus (200) and interpret the data collected from it by mapping the relationship between the four single-axis measurements into a three-dimensional ground reaction force vector. A neural network is capable of approximating this highly non-linear map by optimization of its internal interneuron weights. Using these, the network can infer what the 3D force vector should be. Further details of the machine learning process are given below with reference to FIG. 7.

The ground reaction force measuring system (650) may be implemented for user identification based on gait patterns by means of the machine learning and may be augmented with Internet of Things technologies to connect to the cloud from the computing device (600).

This ground reaction force measuring system (650) has applications for measurement of three-dimensional force that can be extended to various sectors. These include but are not limited to: mining; manufacturing; healthcare; automation; and footwear design.

FIG. 6 illustrates an example of a computing device (600) in which various aspects of the disclosure may be implemented. The computing device (600) may be embodied as any form of data processing device including a personal computing device (e.g. laptop or desktop computer), a server computer (which may be self-contained, physically distributed over a number of locations), a client computer, or a communication device, such as a mobile phone (e.g. cellular telephone), satellite phone, tablet computer, personal digital assistant or the like. Different embodiments of the computing device may dictate the inclusion or exclusion of various components or subsystems described below.

The computing device (600) may be suitable for storing and executing computer program code. The various participants and elements in the previously described system diagrams may use any suitable number of subsystems or components of the computing device (600) to facilitate the functions described herein. The computing device (600) may include subsystems or components interconnected via a communication infrastructure (605) (for example, a communications bus, a network, etc.). The computing device (600) may include one or more processors (610) and at least one memory component in the form of computer-readable media. The one or more processors (610) may include one or more of: CPUs, graphical processing units (GPUs), microprocessors, field programmable gate arrays (FPGAs), application specific integrated circuits (ASICs) and the like. In some configurations, a number of processors may be provided and may be arranged to carry out calculations simultaneously. In some implementations various subsystems or components of the computing device (600) may be distributed over a number of physical locations (e.g. in a distributed, cluster or cloud-based computing configuration) and appropriate software units may be arranged to manage and/or process data on behalf of remote devices.

The memory components may include system memory (615), which may include read only memory (ROM) and random access memory (RAM). A basic input/output system (BIOS) may be stored in ROM. System software may be stored in the system memory (615) including operating system software. The memory components may also include secondary memory (620). The secondary memory (620) may include a fixed disk (621), such as a hard disk drive, and, optionally, one or more storage interfaces (622) for interfacing with storage components (623), such as removable storage components (e.g. magnetic tape, optical disk, flash memory drive, external hard drive, removable memory chip, etc.), network attached storage components (e.g. NAS drives), remote storage components (e.g. cloud-based storage) or the like.

The computing device (600) may include an external communications interface (630) for operation of the computing device (600) in a networked environment enabling transfer of data between multiple computing devices (600) and/or the Internet. Data transferred via the external communications interface (630) may be in the form of signals, which may be electronic, electromagnetic, optical, radio, or other types of signal. The external communications interface (630) may enable communication of data between the computing device (600) and other computing devices including servers and external storage facilities. Web services may be accessible by and/or from the computing device (600) via the communications interface (630).

The external communications interface (630) may be configured for connection to wireless communication channels (e.g., a cellular telephone network, wireless local area network (e.g. using Wi-Fi™), satellite-phone network, Satellite Internet Network, etc.) and may include an associated wireless transfer element, such as an antenna and associated circuitry.

The computer-readable media in the form of the various memory components may provide storage of computer-executable instructions, data structures, program modules, software units and other data. A computer program product may be provided by a computer-readable medium having stored computer-readable program code executable by the central processor (610). A computer program product may be provided by a non-transient computer-readable medium, or may be provided via a signal or other transient means via the communications interface (630).

Interconnection via the communication infrastructure (605) allows the one or more processors (610) to communicate with each subsystem or component and to control the execution of instructions from the memory components, as well as the exchange of information between subsystems or components. Peripherals (such as printers, scanners, cameras, or the like) and input/output (I/O) devices (such as a mouse, touchpad, keyboard, microphone, touch-sensitive display, input buttons, speakers and the like) may couple to or be integrally formed with the computing device (600) either directly or via an I/O controller (635). One or more displays (645) (which may be touch-sensitive displays) may be coupled to or integrally formed with the computing device (600) via a display (645) or video adapter (640).

Figure 7:
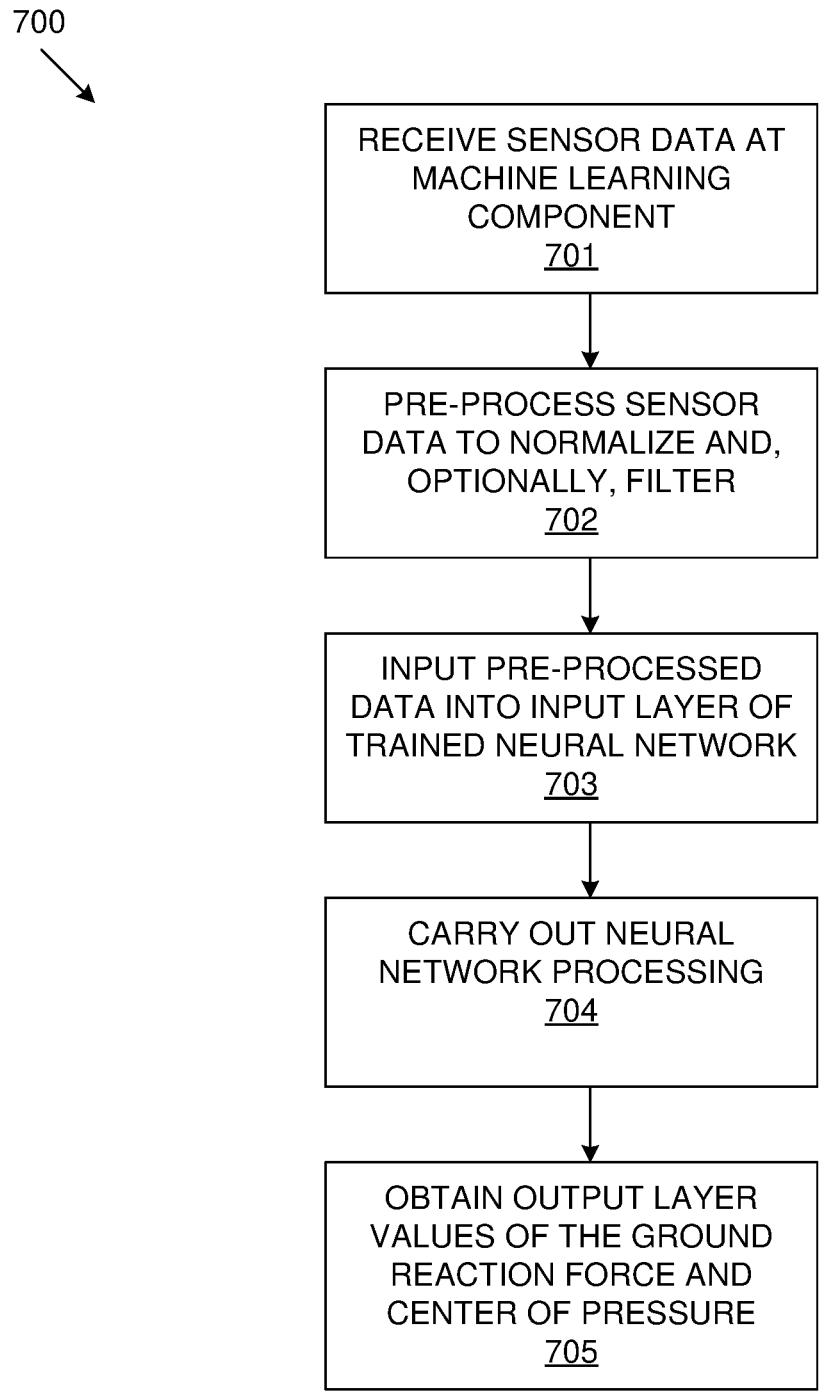
FIG. 7 is a flow diagram showing an example embodiment of a method of processing data by machine learning in accordance with an aspect of the present invention.

Referring to FIG. 7, a flow diagram (700) shows an example embodiment of a computer-implemented method carried out by the measuring system (650) using the data receiving component (651), the pre-processing component (652) and the machine learning component (660). The components may be software components comprising computer instructions stored in memory for carrying out the described method by a processor.

The method is responsible for the processing of raw data captured from the force plate's sensors and using this data to determine the 3D ground reaction force measurement. The center of pressure measurement may also be determined. The center of pressure is a point on a surface through which the resultant force due to pressure passes.

The measuring system (650) receives (701) raw sensor data consisting of time-series measurements from each load cell and temperature sensor. The raw data may be pre-processed (702) including normalization of the data and, optionally, filtering of the data.

The machine learning component (660) in this embodiment is a neural network architecture in the form of a deep neural network. A deep neural network is defined as any neural network having more than a single hidden layer. The network consists of an input layer, multiple hidden layers, and an output layer.

The pre-processed measurements are input (703) as values to the input layer of the neural network. The neural network processing is carried out (704) with the values from the input layer causing neurons in the neural network to activate. Values are obtained (705) at the output layer as a function of the activations in the network. Connections between neurons in the network have weights and biases associated with them which are in turn responsible for determining when certain neurons should activate.

The neural network is trained during a training process, in which, for each set of input values, a set of predetermined output values are compared against the output of the neural network. If the network outputs an incorrect set of outputs, the weights and biases inside the network are then updated such that it will give a closer output to the predetermined output if given the same input again. By subjecting the network to large amounts of examples (for example, 60,000 training samples), it can incrementally learn the mapping from raw data to 3D ground reaction force measurements and center of pressure measurements.

In order to ensure that the results obtained are robust, the trained neural network is tested on data which it has never seen before and the error measurements (for example, in the form of mean squared error or mean absolute error) are recorded as a measure of the network's predictive accuracy. For example, a test case may use approximately 40,000 unseen samples for testing.

The problem which the software solves is that of mapping raw measurements to useful 3D ground reaction force and center of pressure data. This mapping is complex and non-linear due to the need to account for effects such as the bending or warping of the force plate under stress, fluctuations and drift in measurements due to temperature changes, and noise.

While existing high-precision force plates use additional hardware (such as multi-axis load cells) to account for these effects, the described method addresses the problem by accounting for the effects in software while using commercial off-the-shelf hardware. By using a deep neural network, the software learns to counteract the unwanted effects and how to map the raw data to the 3D ground reaction force and center of pressure measurements.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

Any of the steps, operations, components or processes described herein may be performed or implemented with one or more hardware or software units, alone or in combination with other devices. In one embodiment, a software unit is implemented with a computer program product comprising a non-transient computer-readable medium containing computer program code, which can be executed by a processor for performing any or all of the steps, operations, or processes described. Software units or functions described in this application may be implemented as computer program code using any suitable computer language such as, for example, Java™, C++, or Perl™ using, for example, conventional or object-oriented techniques. The computer program code may be stored as a series of instructions, or commands on a non-transitory computer-readable medium, such as a random access memory (RAM), a read-only memory (ROM), a magnetic medium such as a hard-drive, or an optical medium such as a CD-ROM. Any such computer-readable medium may also reside on or within a single computational apparatus, and may be present on or within different computational apparatuses within a system or network.

Flowchart illustrations and block diagrams of methods, systems, and computer program products according to embodiments are used herein. Each block of the flowchart illustrations and/or block diagrams, and combinations of blocks in the flowchart illustrations and/or block diagrams, may provide functions which may be implemented by computer readable program instructions. In some alternative implementations, the functions identified by the blocks may take place in a different order to that shown in the flowchart illustrations.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Finally, throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A ground reaction force plate apparatus comprising:
a plate for receiving a force to be measured as applied by a subject to the plate;
a base support on which a plurality of load cells are provided in an arrangement with only the load cells supporting the plate and with the plate spaced apart from the base support,
wherein each load cell is a sensor with a single sensing axis extending longitudinally along the sensor, wherein the sensor is configured to measure data relating to a force vector applied along the sensing axis when the subject applies the force to the plate;
wherein the single sensing axis of at least one of the sensors is oriented towards a centre of the plate; and
a data collection controller for logging time series measurements of the load cells over a time period in which the subject applies the force to the plate;
wherein the time series measurements of the load cells are processed to calculate three-dimensional components of the force applied by the subject to the plate over the time period.

2. The apparatus as claimed in claim 1, including: a plurality of position sensors for detecting a position of the subject applying the force to the plate; and wherein the data collection controller is configured to log time series measurements of the position sensors over the time period in which the subject applies the force to the plate.

3. The apparatus as claimed in claim 2, wherein the position sensors are provided in the form of a grid of mechanical switches or in the form of optical position sensors.

4. The apparatus as claimed in claim 1, including: a temperature sensor for measuring an ambient temperature at a time of the load cell measurements and including the ambient temperature in the logged time series measurements of the load cells.

5. The apparatus as claimed in claim 1, wherein the plate is a rectangular plate with four load cells supporting the plate, or is a hexagonal plate with six load cells supporting the plate.

6. The apparatus as claimed in claim 1 wherein the sensing axes of at least some of the load cells are provided at an angle of between 30 degrees and 60 degrees to a plane of the plate.

7. The apparatus as claimed in claim 1, wherein a plurality of plates is provided with the plates disposed in an adjacent arrangement for sensing data of a subject applying sequential forces to the plurality of plates.

8. The apparatus as claimed in claim 1, wherein each load cell is provided towards an edge of the plate.

9. The apparatus as claimed in claim 1, wherein each load cell is associated with a side of the plate or with a corner of the plate.

10. The apparatus as claimed in claim 1, wherein the sensing axes of at least two of the load cells are oriented in different directions.

11. The apparatus as claimed in claim 1, wherein at least three load cells are provided.

12. The apparatus as claimed in claim 11, wherein the sensing axes of three of the at least three load cells are at right angles to each other.

\* \* \* \* \*